US012778782B2

(12) United States Patent
Grundmann et al.

(10) Patent No.: US 12,778,782 B2
(45) Date of Patent: Nov. 3, 2026

(54) BANDAGE OR ORTHOSIS WITH ABDOMINAL SUPPORT FUNCTION

(71) Applicant: BAUERFEIND AG, Zeulenroda-Triebes (DE)

(72) Inventors: Madlin Grundmann, Zeulenroda-Triebes (DE); Beatrix Bauerfeind-Johnson, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 104 days.

(21) Appl. No.: 18/994,049

(22) PCT Filed: Jul. 13, 2023

(86) PCT No.: PCT/EP2023/069482
§ 371 (c)(1),
(2) Date: Jan. 13, 2025

(87) PCT Pub. No.: WO2024/017756
PCT Pub. Date: Jan. 25, 2024

(65) Prior Publication Data

US 2026/0248632 A1 Aug. 27, 2026

(30) Foreign Application Priority Data

Jul. 18, 2022 (DE) ......................... 102022117881.1

(51) Int. Cl.
*A61F 5/02* (2006.01)

(52) U.S. Cl.
CPC .................................... *A61F 5/028* (2013.01)

(58) Field of Classification Search
CPC .. A61F 5/02; A61F 5/022; A61F 5/024; A61F 5/028; A61F 5/03; A61F 5/3746; A61F 5/3753; A61F 13/148; A61F 13/68
See application file for complete search history.

(56) References Cited

U.S. PATENT DOCUMENTS

| | | | | | |
|---|---|---|---|---|---|
| 344,065 | A | | 6/1886 | Teufel | |
| 1,939,811 | A | * | 12/1933 | Guenther | A61F 5/03 450/137 |
| 2,476,029 | A | * | 7/1949 | Dawson | A41C 1/08 450/138 |
| 3,096,760 | A | * | 7/1963 | Nelkin | A61F 5/028 128/95.1 |

(Continued)

FOREIGN PATENT DOCUMENTS

| | | | |
|---|---|---|---|
| EP | 2965726 | A1 | 1/2016 |
| EP | 3242490 | A1 | 11/2017 |
| WO | 2014006521 | A1 | 1/2014 |

OTHER PUBLICATIONS

European Patent Office acting as International Searching Authority, "International Search Report and Written Opinion," for International Application No. PCT/EP2023/069482, Oct. 19, 2023.

(Continued)

*Primary Examiner* — Kari K Rodriquez
(74) *Attorney, Agent, or Firm* — Dentons Durham Jones Pinegar; Sarah W. Matthews

(57) ABSTRACT

The present invention relates to a bandage or orthosis, in particular a pregnancy orthosis.

12 Claims, 5 Drawing Sheets

(56) References Cited

U.S. PATENT DOCUMENTS

Figure 1:
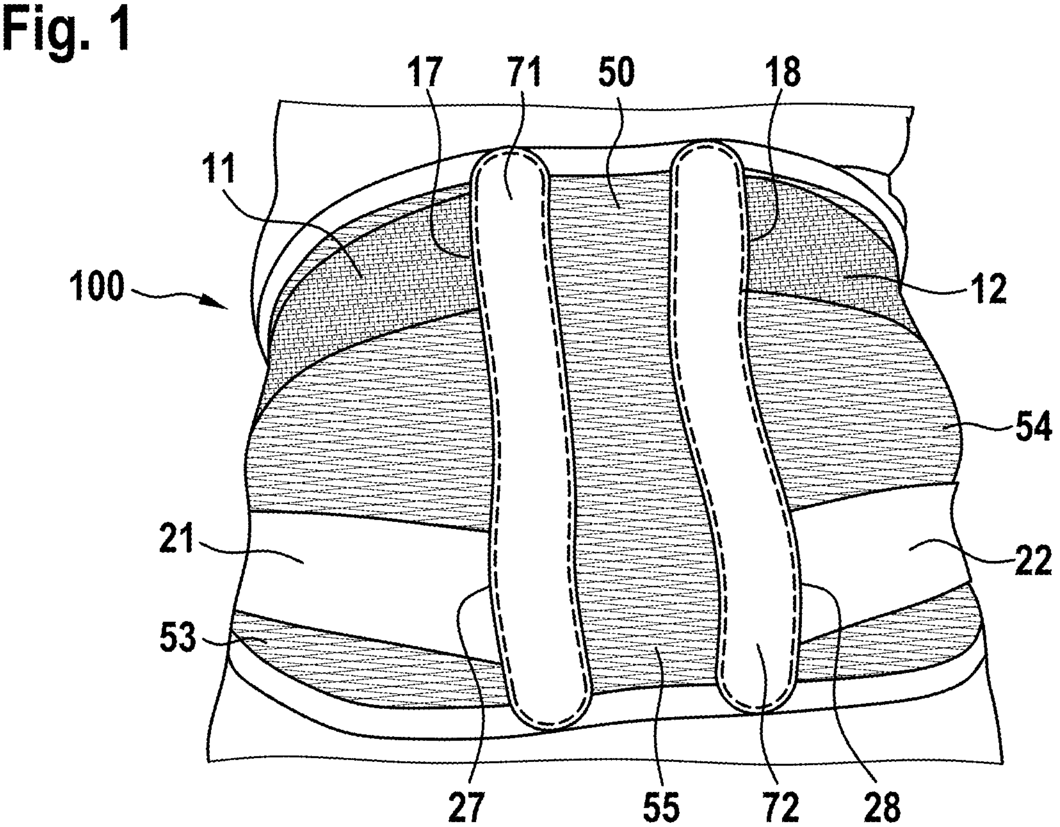

| | | | | | |
|---|---|---|---|---|---|
| 3,926,183 | A * | 12/1975 | Spiro | A61F 5/028 450/94 |
| 5,267,948 | A * | 12/1993 | Elliott | A61F 5/03 128/869 |
| 5,634,891 | A * | 6/1997 | Beczak, Sr. | A61F 5/028 450/119 |
| 6,071,175 | A | 6/2000 | Working, III | |
| 6,099,490 | A * | 8/2000 | Turtzo | A61F 5/028 2/311 |
| 6,503,215 | B1 * | 1/2003 | Reinhardt | A61F 5/028 602/41 |
| 10,842,660 | B1 * | 11/2020 | Norstrem | A61N 1/0484 |
| 2013/0072087 | A1 | 3/2013 | Chen | |
| 2021/0259873 | A1 | 8/2021 | Lyzhyn | |
| 2022/0175052 | A1 | 6/2022 | Dillard | |

OTHER PUBLICATIONS

German Patent Office, "Search Report," for German Application No. 10 2022 117 881.1.

* cited by examiner

BANDAGE OR ORTHOSIS WITH ABDOMINAL SUPPORT FUNCTION

CROSS-REFERENCE TO RELATED APPLICATION

A claim is made for priority under 35 U.S.C. 365(b) to the 13 Jul. 2023 filing date of International Application No. PCT/EP2023/069482 ("the '482 PCT Application"), titled BANDAGE OR ORTHOSIS WITH ABDOMINAL SUPPORT FUNCTION which claims priority to German Patent Application No. 10 2022 117 881.1 ("the '881.1 German Priority Application), filed 18 Jul. 2022. The entire disclosures of the '482 PCT Application and '881.1 German Priority Application are hereby incorporated by reference.

The present invention relates to a bandage or orthosis which can be used in particular during pregnancy.

Due to weight gain, for example during pregnancy, caused by the growth of the child, back pain may occur. It can also lead to the formation of a hollow back because the pelvis is "tilted" during pregnancy to maintain balance. More specifically, it can lead to problems with the facet joints in the lumbar region and in the pelvis with the sacroiliac joint (SIJ) or the cross-iliac joint and the symphysis. Due to the additional weight to be carried the stress on the spine and the sacroiliac joint increases. Due to the hormonal change during pregnancy, the tendons and ligaments in the hips become softer and the pelvis begins to "slide apart", which is accompanied by symphysis pain.

Conventional back orthoses work according to a "3-point system" that applies force at the anatomical points: (1) abdominal area, (2) upper back area and (3) lower back area, wherein the main focus of the application of force is on points 2 and 3—thus the back.

The underlying technical problem of the present invention is to provide an improved bandage or orthosis, for example a pregnancy orthosis, which can in particular relieve the spine and the sacroiliac joint as well as the symphysis, can compensate somewhat for the resulting excessive hollow back and additionally stabilise the pelvis in order to alleviate the SI joint and symphysis pain.

The present invention solves the underlying problem by means of the subject matter of claim 1.

The present invention relates in particular to a bandage or orthosis for the lumbar region, having

- an elongated, flat base body having a first end region, a second end region, a central region and a first intermediate region between the first end region and the central region and a second intermediate region between the second end region and the central region, wherein the first end region and the second end region are reversibly connectable to each other,
- a first elongated abdominal lifting element and a second elongated abdominal lifting element, each having a first end and
- a first elongated tensioning element and a second elongated tensioning element, each having a first end,
- wherein the first intermediate region and the second intermediate region each have a deflecting element or wherein the first end region and the second end region each have a deflecting element, wherein the first abdominal lifting element is located state in the central region of the base body in the worn state above the first tensioning element and wherein the second abdominal lifting element is located in the central region of the base body in the worn state above the second tensioning element, wherein the first tensioning element runs freely movable in the direction of the first end region of the base body and the second tensioning element runs freely movable in the direction of the second end region of the base body, wherein the first tensioning element ends with the second end at the first central region of the base body and the second tensioning element ends with the second end at the second central region of the base body, and wherein the first end of the first tensioning element and the first end of the second tensioning element each have a deflecting element, wherein the first abdominal lifting element runs from the central region of the base body to the deflecting element of the first intermediate region or of the first end region and is deflected there, and the second abdominal lifting element runs from the central region of the base body to the deflecting element of the second intermediate region or of the second end region and is deflected there, wherein the first abdominal lifting element runs from the deflecting element of the first intermediate region or of the first end region to the deflecting element of the first tensioning element and is deflected there, and the second abdominal lifting element runs from the deflecting element of the second intermediate region or of the second end region to the deflecting element of the second tensioning element and is deflected there, wherein the first abdominal lifting element runs from the deflecting element of the first tensioning element in the direction of at least one of the end regions of the base body and wherein the second abdominal lifting element runs from the deflecting element of the second tensioning element in the direction of at least one of the end regions of the base body, and wherein the first end of the first abdominal lifting element and the first end of the second abdominal lifting element are each reversibly attachable onto the first end region of the base body and/or onto the second end region of the base body and/or onto the first end of the other abdominal lifting element respectively.

In a preferred embodiment, the first abdominal lifting element and the second abdominal lifting element and/or the first tensioning element and the second tensioning element are each connected with a second end to the central region of the base body and wherein preferably the connection of the second end of the first abdominal lifting element to the central region of the base body in the worn state is located above the connection of the second end of the first tensioning element to the central region of the base body and wherein the connection of the second end of the second abdominal lifting element to the central region of the base body in the worn state is located above the connection of the second end of the second tensioning element to the central region of the base body.

In a preferred embodiment, the first and the second abdominal lifting elements are connected to each other in the central region of the base body and/or the first and the second tensioning elements are connected to each other in the central region of the base body.

In a preferred embodiment, the abdominal lifting elements have a greater total elasticity than the tensioning elements.

In a preferred embodiment, the abdominal lifting elements and/or the tensioning elements are straps.

In a preferred embodiment, the deflecting elements of the tensioning elements are configured as buckles.

In a preferred embodiment, the base body has stabilising rods in the central region and/or in the intermediate region.

In a preferred embodiment, the end regions of the base body are designed as a hook-and-loop fastener.

In a preferred embodiment, the end regions connectable to each other of the base body are at least 15 cm long. The end regions of the base body can also be shorter than 15 cm. The end regions can also be variably connectable to each other by means of an additional hook-and-loop strip (similar to a "fish-mouth hook-and-loop" strap extension).

In a preferred embodiment, pads and/or heat cushions and/or cold cushions can be assigned to the base body.

The abdominal lifting element can also have different regions with different elasticity/stretch. The abdominal lifting element can also have different regions with different elasticity. The abdominal lifting element can also have different regions with different stretch. The abdominal lifting element can also have different regions with different elasticity and stretch. For example, a two-part strap with different stretches can be used.

Preferably, the bandage or the orthosis according to the invention is a pregnancy bandage or a pregnancy orthosis.

The present invention is explained in more detail by means of the following example and figures, wherein this is not to be understood limiting.

Figure 2:
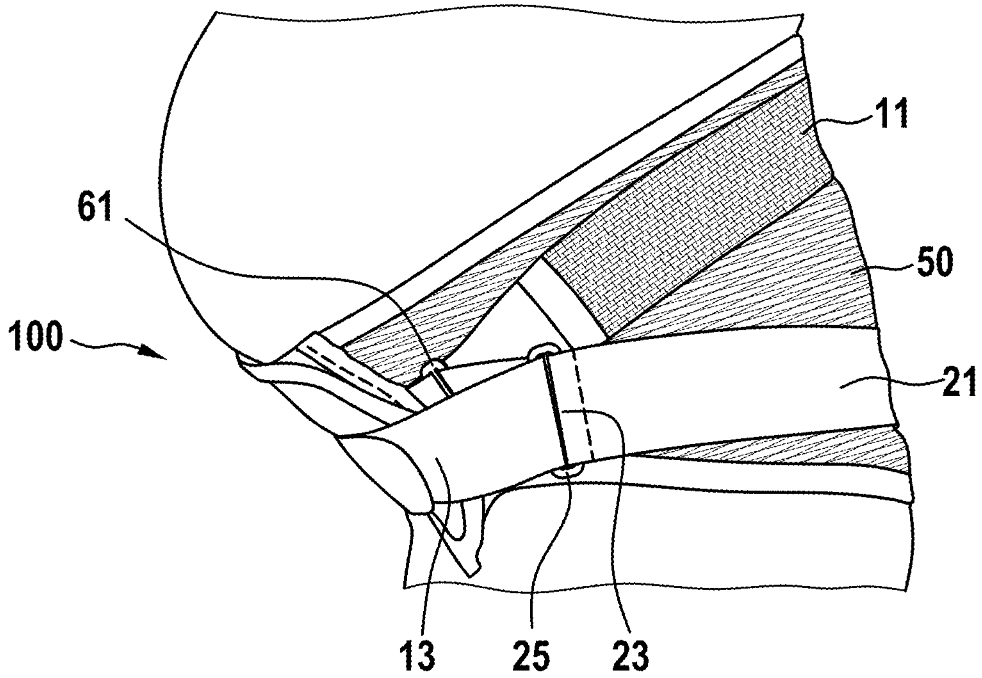
Figure 3:
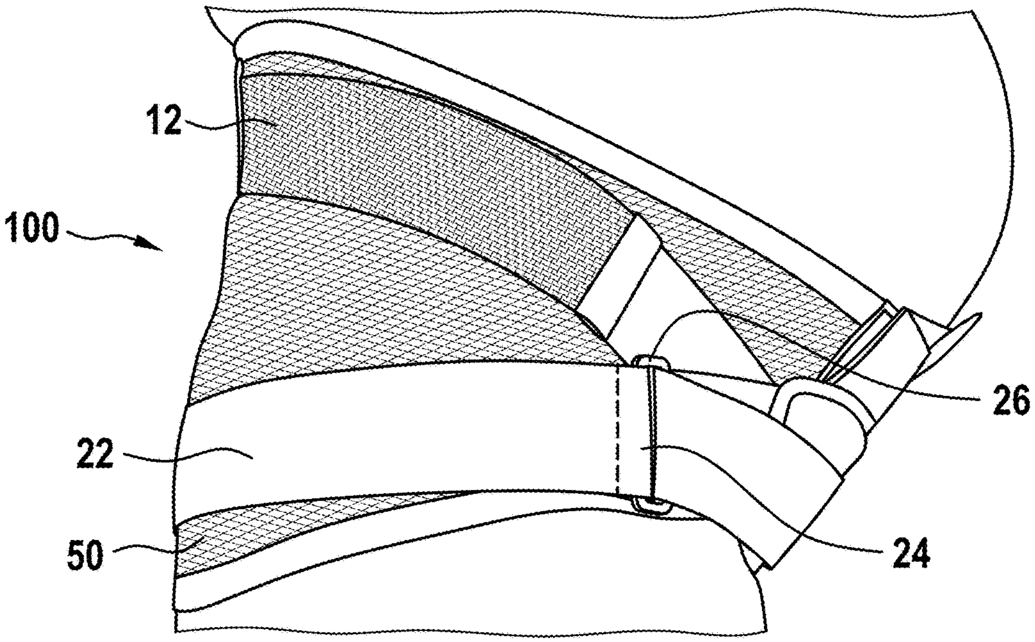
Figure 4:
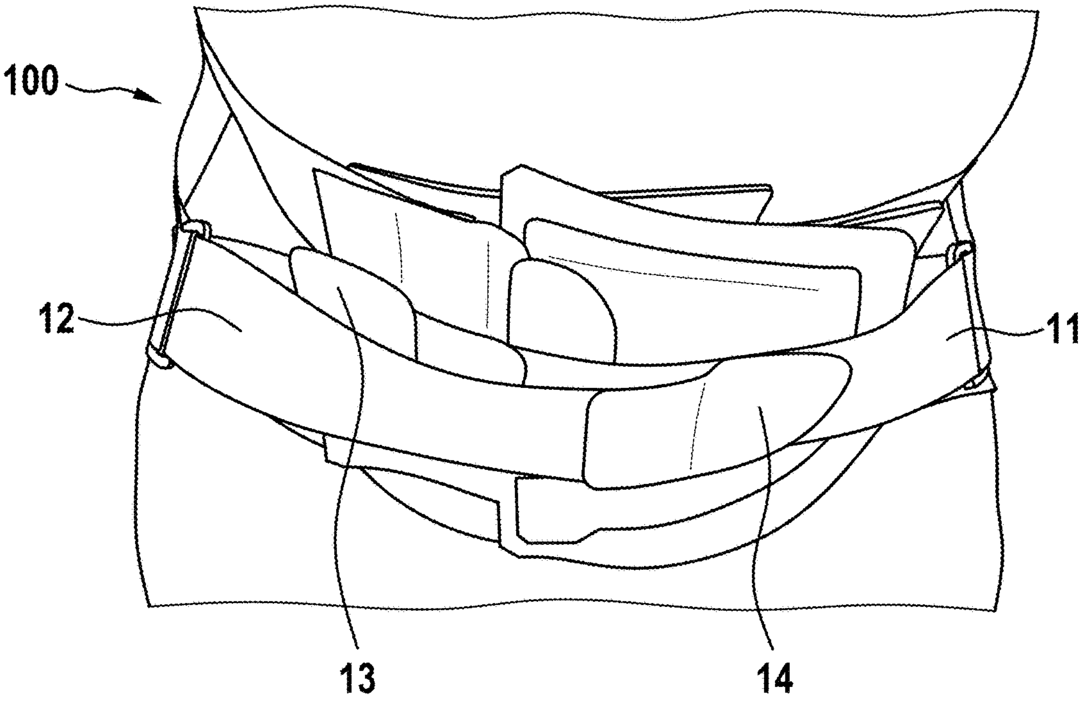
Figure 5:
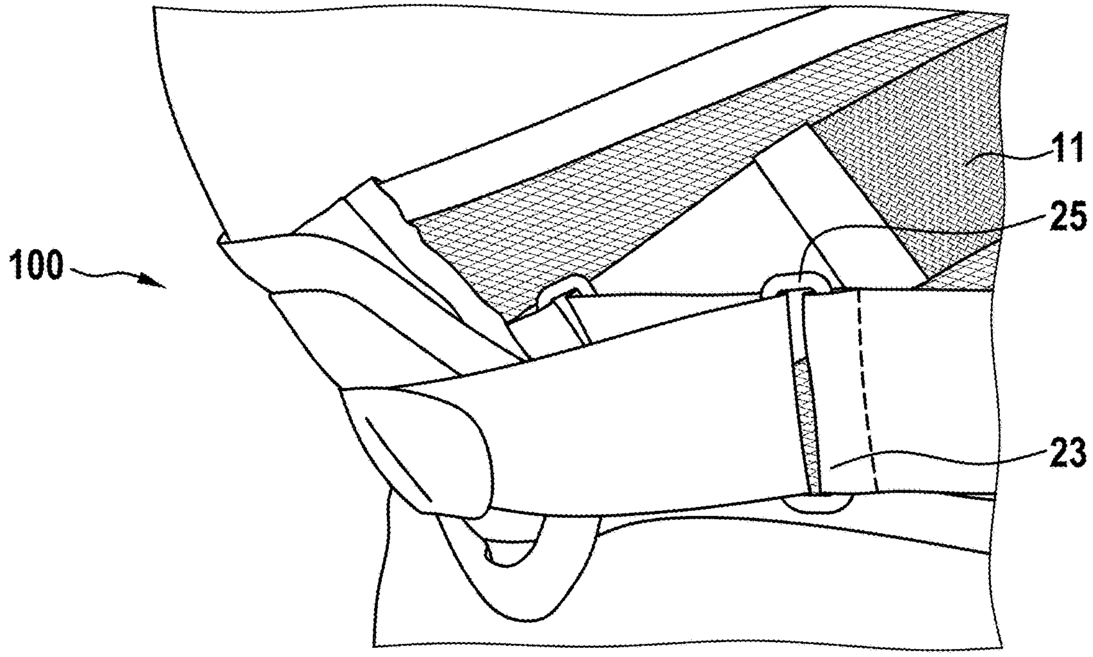

Showing:

FIG. 1: A bandage or an orthosis according to the invention, here as a pregnancy orthosis, back view, FIG. 2: The bandage or the orthosis according to the invention of FIG. 1, left side view, FIG. 3: The bandage or the orthosis according to the invention of FIG. 1, right side view, FIG. 4: The bandage or the orthosis according to the invention of FIG. 1, front view, FIG. 5: The bandage or the orthosis according to the invention of FIG. 1, left side view, FIG. 6: Detailed view of an alternative embodiment of the bandage or the orthosis, FIG. 7: Detail of the central region of a further alternative embodiment of the bandage or the orthosis of FIG. 1, FIG. 8: Total view of the bandage or the orthosis of FIG. 1.

The figures show a bandage or an orthosis (100) for the lumbar region, here in a preferred embodiment of a pregnancy orthosis, having an elongated, flat base body (50), having a first end region (51), a second end region (52), a central region (55) and a first intermediate region (53) between the first end region (51) and the central region (55) and a second intermediate region (54) between the second end region (52) and the central region (55), wherein the first end region (51) and the second end region (52) are reversibly connectable to each other, a first elongated abdominal lifting element (11) and a second elongated abdominal lifting element (12) each having a first end (13,14), and a first elongated tensioning element (21) and a second elongated tensioning element (22) each having a first end (23,24), wherein the first intermediate region (53) and the second intermediate region (54) each have a deflecting element (61,62) or wherein the first end region (51)) and the second end region (52) of the base body (50) each have a deflecting element, wherein the first abdominal lifting element (11) is located in the central region (55) of the base body (50) in the worn state above the first tensioning element (21) and wherein the second abdominal lifting element (12) is located in the central region (55) of the base body (50) in the worn state above the second tensioning element (22), wherein the first tensioning element (21) runs freely movable in the direction of the first end region (51) of the base body (50) and the second tensioning element (22) runs freely movable in the direction of the second end region (52) of the base body (50), wherein the first tensioning element (21) ends with the first end (23) at the first intermediate region (53) of the base body (50), and the second tensioning element (22) ends with the first end (24) at the second intermediate region (54) of the base body (50), and wherein the first end (23) of the first tensioning element (21) and the first end (24) of the second tensioning element (22) each have a deflecting element (25,26), wherein the first abdominal lifting element (11) runs from the central region (55) of the base body (50) to the deflecting element (61) of the first intermediate region (53) or of the first end region (51) and is deflected there, and the second abdominal lifting element (12) runs from the central region (55) of the base body (50) to the deflecting element (62) of the second intermediate region (54) or of the second end region (52) and is deflected there, wherein the first abdominal lifting element (11) runs from the deflecting element (61) of the first intermediate region (53) or of the first end region (51) to the deflecting element (25) of the first tensioning element (21) and is deflected there, and the second abdominal lifting element (12) runs from the deflecting element (62) of the second intermediate region (54) or of the second end region (52) to the deflecting element (26) of the second tensioning element (22) and is deflected there, wherein the first abdominal lifting element (11) runs from the deflecting element (25) of the first tensioning element (21) in the direction of at least one of the end regions (51,52) of the base body (50), and wherein the second abdominal lifting element (12) runs from the deflecting element (26) of the second tensioning element (22) in the direction of at least one of the end regions (51,52) of the base body (50), and wherein the first end (13) of the first abdominal lifting element (11) and the first end (14) of the second abdominal lifting element (12) are each reversibly attachable onto the first end region (51) of the base body (50) and/or onto the second end region (52) of the base body (50) and/or onto the first end (14,13) of the other abdominal lifting element (12,11) respectively. The first abdominal lifting element (11) and the second abdominal lifting element (12) and/or the first tensioning element (21) and the second tensioning element (22) are each connected with a second end (17, 18, 27, 28) to the central region (55) of the base body (50), wherein the connection of the second end (17) of the first abdominal lifting element (11) to the central region (55) of the base body (50) in the worn state is located above the connection of the second end (27) of the first tensioning element (21) to the central region (55) of the base body (50), and wherein the connection of the second end (18) of the second abdominal lifting element (12) to the central region (55) of the base body (50) in the worn state is located above the connection of the second end (28) of the second tensioning element (22) to the central region (55) of the base body (50). The base body (50) can have stabilising rods (71,72) in the central region and/or in the intermediate region.

Figure 6:
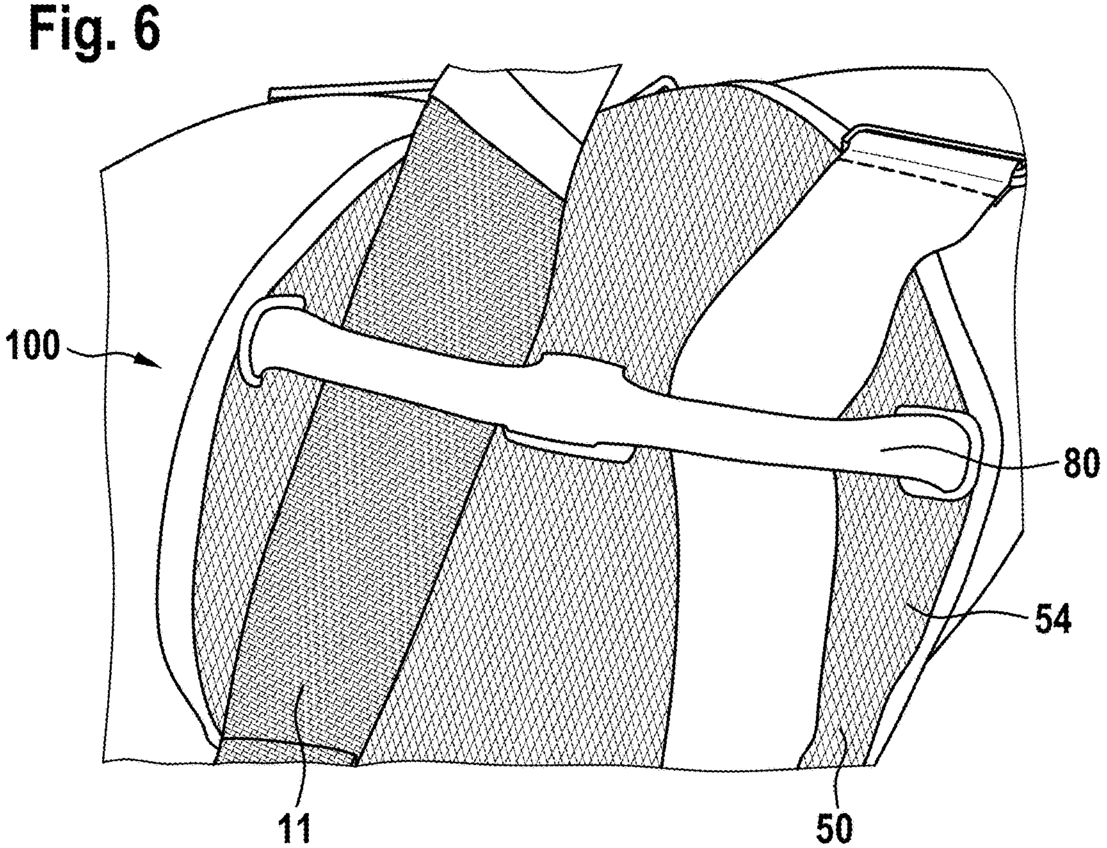

In the embodiment shown in FIG. 6, the first and second abdominal lifting elements are connected to each other in the central region of the base body and the first and second tensioning elements are connected to each other in the central region of the base body. The abdominal lifting elements and the tensioning elements are guided and held by guiding elements (80) located on the base body.

Figure 7:
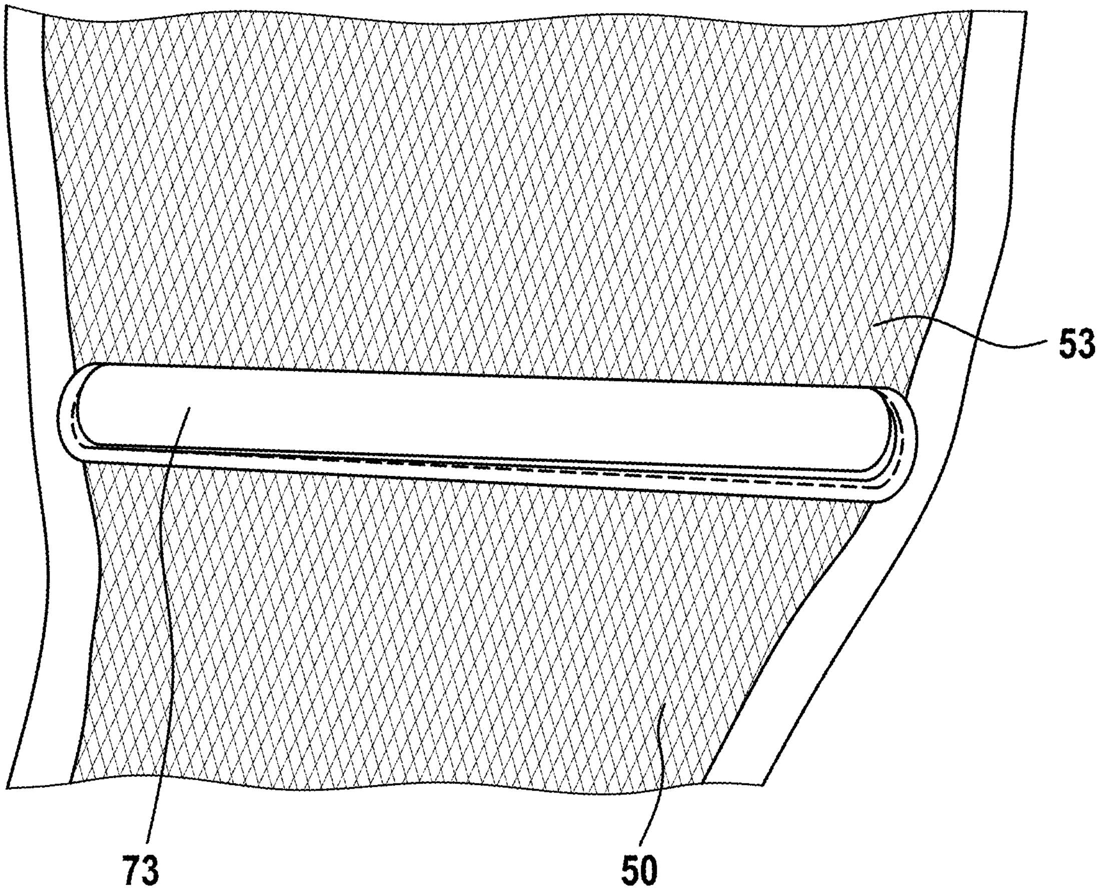
Figure 8:
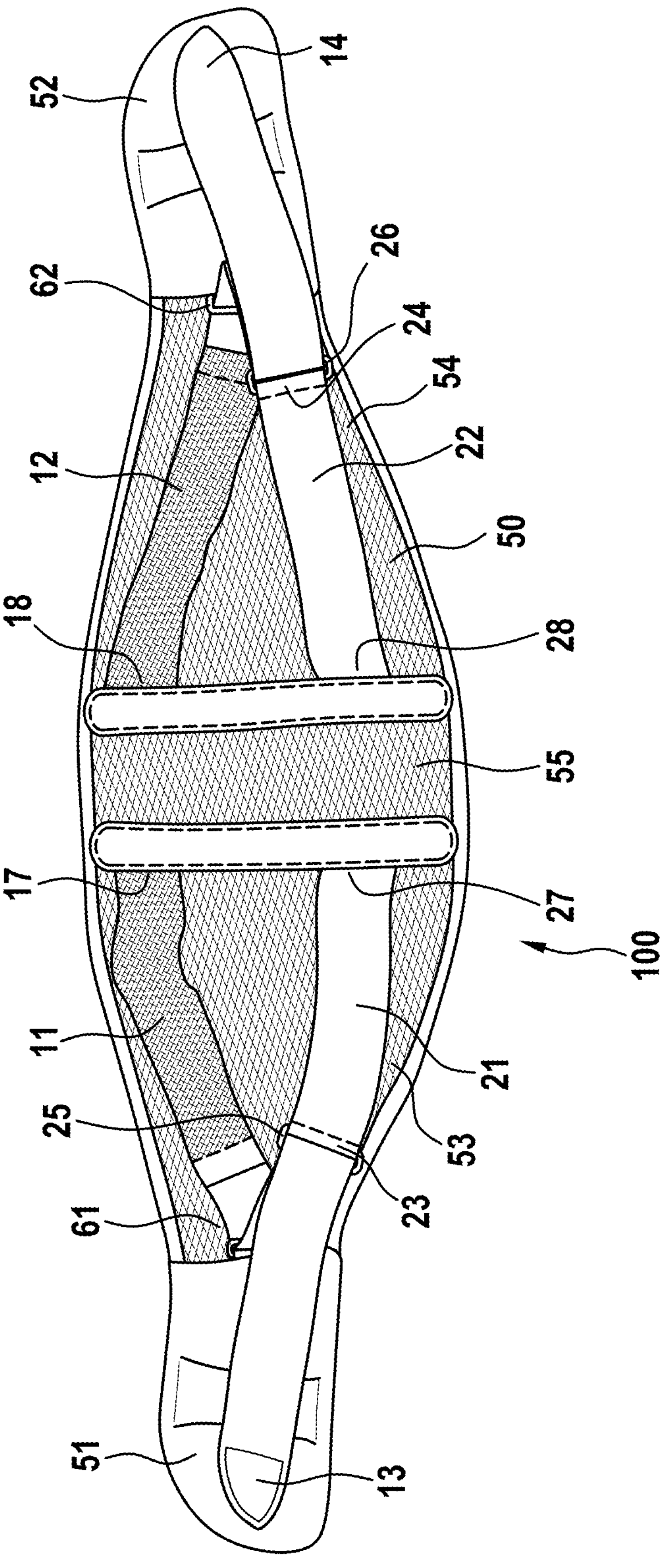

FIG. 7 shows a further optional embodiment in which further stabilising rods (73) are provided namely in the intermediate regions (53). Of course, an additional stabilising rod of the same kind is also located in the second intermediate region.

In order to relieve the spine and the sacroiliac joint as well as the symphysis, the abdomen can be "lifted" using the pregnancy orthosis according to the invention and gently guided back to the spine in order to compensate somewhat for the resulting excessive hollow back—in particular, to be supported from the lower abdomen. This support is provided by the new elastic upper of the two straps, which forms the counterbearing, so to speak, for the lower abdomen on the opposite side. Additionally, the pelvis should be stabilised to alleviate the SI joint and symphysis pain. This task is performed by the second, lower and inelastic strap. The orthosis thus fulfils two tasks separately. Thanks to the principle of combining elastic and inelastic tension straps or strap parts, their sliding attachment on top of each other and the 180-degree change of direction when force is applied, it is possible for the first time to allow the tension applied to act primarily on the lower abdomen. The three points of application of our new back orthosis are the upper and lower strap positions on the back, as well as the abdominal area of the orthosis.

Structure of the Exemplary Pregnancy Orthosis:

A. Base body: circumferential, perforated base strap made of elastic knitted fabric. The base strap consists of a flexible carrier material. In the region of the spine, two anatomically shaped stabilising rods are preferably introduced parallel to each other. These are not essential for the function of the new aid, but are common today. The rods have the effect of spanning the orthosis in its height and preventing it from collapsing. Additionally, they serve as "anchor points" for the tension strap system. Please note that the tension straps could be repositionably attached there without the rods, where the rods are positioned—the function of the new orthosis is ensured even without the two rods. The rods can be seen in FIG. 1. The elastic base strap region lying between the two rods could alternatively be configured to be non-elastic without any significant functional impairment. In the present example, this elastic region provides better size coverage and better adaptation to the body shape. Instead of the rods, the straps could also be fixed onto the base strap via strap guides. It is also preferable that the two tension straps could also be configured circumferentially, so that they do not have to be separated and attached in the region of the spine.

B. Abdominal lifting elements: upper strap (strap 1) The "upper elastic strap" or strap 1 has the task of lifting the abdomen. It runs from the spine towards the abdominal closure (see FIG. 2). At the abdominal closure, it is deflected and runs back towards the spine. However, the strap here runs at a different angle than its incidence angle, resulting in a V-shape of the strap in the deflection region. On its way in the direction of the spine, the upper strap meets the lower strap, at the end of which a further deflecting element is attached. In this second deflecting element, the upper strap is deflected a second time, which results in a Z-shaped course. After this second deflection, the upper strap runs again in the direction of the abdominal closure. The free end of the upper strap is then attached onto the abdominal closure using a hook-and-loop fastener. Other types of attachements can also be used for this purpose. Strap 1 must be made of a more flexible material than strap 2. As can be seen in the figures, strap 1 can have one or more elastic and non-elastic sections in its course. Preferably, a first region of strap 1 is elastic starting from the spine. In the region of the deflections, a less elastic strap is advantageous because such a strap slides better through the deflections. The straps can also be implemented as cable-pull, Bowden cables, flat belts or similar. Additionally, strap guides or stabilising rods can be attached to the orthosis to better span the carrier material, as shown in FIGS. 6 & 7. The elasticity of the strap allows the abdomen to "bounce", for example when climbing stairs.

C. Tension straps: lower strap (strap 2) The "lower strap" or tension strap 2, which has the function of stabilising the pelvis, can preferably have less elasticity than strap 1. Strap 2 runs from its fixation in the region of the spine in the direction of the abdominal closure. However, strap 2 ends before the abdominal closure, as it is attached directly onto tension strap 1 by means of a deflecting element. At its end, there is a deflecting element in which strap 1 is deflected. Strap 1 thus tensions strap 2. This "Y-shaped" strap tensioning principle with deflecting element has the significant advantage that the 2nd tension strap can slip when a tensile force is applied to the elastic tension strap and thus find the ideal position.

Applying the pregnancy orthosis: In the first step, the abdominal closure of the base carrier is closed on the underside of the abdomen. The hook-and-loop region of the abdominal closure is designed so that the orthosis can practically "grow" with the pregnancy, because the effective range of the hook-and-loop fastener covers a good 20 cm in circumference. In a second step, the elastic tension strap 1 is pulled away from the body at an angle of about 90° and thus tensioned. This is how the abdominal lifting function is adjusted, since in this tensioning position only the tension strap 1 is initially tensioned. When the desired tension is reached, the tension strap 1 is attached to the abdominal closure, starting from the 90° position. With this change of angle, the tensile force applied is now also transferred to the inelastic tension strap 2. Once the ends of the tension strap 1 have been attached onto the base strap, the entire system is tensioned and the circular force is circumferentially "balanced" in both tension straps. At the same time, the elastic tension strap 1 blocks itself due to the 180-degree deflection and cannot be tensioned further. Thus, the pelvis can be stabilised as desired with the help of the tension strap 1. The further the strap ends are now pulled towards the abdominal closure, the more A) the lower abdomen is lifted and B) the pelvis is stabilised.

Carrier base strap (currently: net-like knitted fabric), which can be elastic or non-elastic. In the preferred embodiment, the carrier material is elastic for a better fit on the body. The carrier material can have different zones with differing elasticity. An alternative design provides for non-elastic zones in the region of the spine. The base strap can be provided with or without vertical stabilising rods in the back region. The supplementary tension strap system consists of two circular tension straps (upper and lower strap) with two deflecting elements each, wherein one of the straps has a deflecting element at both of its ends. The other strap has hook-and-loop or similar fasteners at its ends. Both straps are applied to the carrier material in the region of the spine. Strap 1, the "upper strap", is deflected twice, resulting in a Z-shaped strap course. The first deflection occurs in the region of the abdominal closure. The second deflection occurs over strap 2, the "lower strap".

Strap 1, the "upper strap", thus the abdominal lifting element, can have zones with different elasticity. Regardless of the elasticity of the individual zones, strap 1 is configured to be just as elastic as strap 2 or more elastic than strap 2. Strap 1 can also be a one piece of elastic material.

The "lower strap" (strap 2), thus the tensioning element, is preferably inelastic. It is attached in the region of the spine and below strap 1. A deflecting element is attached to its free end, through which Strap 1 runs.

The orthosis has at least one strap system. For better application and symmetry, preferably two strap systems are provided. This means that there is a strap system on each side of the orthosis.

The sliding surfaces of the deflecting elements can be slightly "interlocked" to make it more difficult for the strap to "slip" at certain angles of pull. This reinforces the selective tensioning of straps 1 & 2.

The inelastic lower tension strap 2 is connected to the elastic tension strap 1 via a buckle. This connection, which allows the inelastic tension strap 2 to "run along", is the essential element of the pregnancy orthosis according to the invention.

Stabilising rods can be attached to the orthosis at various positions. On the one hand, this has the function of spanning the orthosis carrier material. On the other hand, it allows the forces of the straps to be better transferred to the orthosis.

Abdominal closure elements are attached to the ends of the carrier material. These make it possible to close the orthosis and provide some leeway for the growing abdominal girth.

It is possible to integrate pads as an upgrade option. Additionally or alternatively, cold or heat cushions can be integrated into the bandage or orthosis.

The invention claimed is:

1. An orthosis or a bandage for the lumbar region, comprising:

an elongated, flat base body, having a first end region, a second end region, a central region and a first intermediate region between the first end region and the central region and a second intermediate region between the second end region and the central region, wherein the first end region and the second end region are reversibly connectable to each other, a first elongated abdominal lifting element and a second elongated abdominal lifting element, each having a first end, and a first elongated tensioning element and a second elongated tensioning element, each having a first end, wherein the first intermediate region and the second intermediate region each have a deflecting element or wherein the first end region and the second end region of the base body each have a deflecting element, wherein the first elongated abdominal lifting element is located in the central region of the base body in a worn state above the first tensioning element and wherein the second elongated abdominal lifting element is located in the central region of the base body in the worn state above the second tensioning element, wherein the first tensioning element runs freely movable in the direction of the first end region of the base body and the second tensioning element runs freely movable in the direction of the second end region of the base body, wherein the first tensioning element ends with the first end at the first intermediate region of the base body, and the second tensioning element ends with the first end at the second intermediate region of the base body, and wherein the first end of the first tensioning element and the first end of the second tensioning element each have a deflecting element, wherein the first elongated abdominal lifting element runs from the central region of the base body to the deflecting element of the first intermediate region or of the first end region and is deflected there, and the second elongated abdominal lifting element runs from the central region of the base body to the deflecting element of the second intermediate region or of the second end region and is deflected there, wherein the first abdominal elongated lifting element runs from the deflecting element of the first intermediate region or of the first end region to the deflecting element of the first tensioning element and is deflected there, and the second elongated abdominal lifting element runs from the deflecting element of the second intermediate region or of the second end region to the deflecting element of the second tensioning element and is deflected there, wherein the first abdominal elongated lifting element runs from the deflecting element of the first tensioning element in the direction of at least one of the end regions of the base body and wherein the second elongated abdominal lifting element runs from the deflecting element of the second tensioning element in the direction of at least one of the end regions of the base body, and wherein the first end of the first elongated abdominal lifting element and the first end of the second elongated abdominal lifting element are each reversibly attachable onto the first end region of the base body and/or onto the second end region of the base body and/or onto the first end of the other abdominal lifting element respectively.

2. The orthosis or the bandage of claim 1, wherein the first elongated abdominal lifting element and the second elongated abdominal lifting element and/or the first tensioning element and the second tensioning element are each connected with a second end to the central region of the base body and wherein preferably the connection of the second end of the first elongated abdominal lifting element to the central region of the base body in the worn state is located above the connection of the second end of the first tensioning element to the central region of the base body and wherein the connection of the second end of the second elongated abdominal lifting element to the central region of the base body in the worn state is located above the connection of the second end of the second tensioning element to the central region of the base body.

3. The orthosis or the bandage of claim 1, wherein the first and the second elongated abdominal lifting elements are connected to each other in the central region of the base body and/or the first and the second tensioning elements are connected to each other in the central region of the base body.

4. The orthosis or the bandage of claim 1, wherein the first and the second elongated abdominal lifting elements have a greater total elasticity than the tensioning elements.

5. The orthosis or the bandage of claim 1, wherein the first and the second elongated abdominal lifting elements and/or the tensioning elements are straps.

6. The orthosis or the bandage of claim 1, wherein the deflecting elements of the tensioning elements are configured as buckles.

7. The orthosis or the bandage of claim 1, wherein the base body has stabilising rods in the central region and/or in the intermediate region.

8. The orthosis or the bandage of claim 1, wherein the end regions of the base body are designed as a hook-and-loop fastener.

9. The orthosis or the bandage of claim 1, wherein pads and/or heat cushions and/or cold cushions can be assigned to the base body.

10. The orthosis or the bandage of claim 1, wherein at least one of the first and second elongated abdominal lifting elements, has different regions with different elasticity and/or stretch.

11. The orthosis or the bandage of claim 1, wherein the orthosis or the bandage is a pregnancy orthosis or a pregnancy bandage.

12. An orthosis to be worn on a user's lumbar region, the orthosis comprising:

an elongated, flat base body, having a first end region, a second end region, a central region and a first intermediate region between the first end region and the central region and a second intermediate region between the second end region and the central region, wherein the first end region and the second end region are reversibly connectable to each other;

a first abdominal lifting element and a second abdominal lifting element, each having a first end; and a first elongated tensioning element and a second elongated tensioning element, each having a first end;

wherein the first intermediate region and the second intermediate region each have a deflecting element or wherein the first end region and the second end region of the base body each have a deflecting element, wherein the first abdominal lifting element is located in the central region of the base body in a worn state above the first tensioning element and wherein the second abdominal lifting element is located in the central region of the base body in the worn state above the second tensioning element, wherein the first tensioning element runs freely movable in the direction of the first end region of the base body and the second tensioning element runs freely movable in the direction of the second end region of the base body, wherein the first tensioning element ends with the first end at the first intermediate region of the base body, and the second tensioning element ends with the first end at the second intermediate region of the base body, and wherein the first end of the first tensioning element and the first end of the second tensioning element each have a deflecting element, wherein the first abdominal lifting element runs from the central region of the base body to the deflecting element of the first intermediate region or of the first end region and is deflected there, and the second abdominal lifting element runs from the central region of the base body to the deflecting element of the second intermediate region or of the second end region and is deflected there, wherein the first abdominal lifting element runs from the deflecting element of the first intermediate region or of the first end region to the deflecting element of the first tensioning element and is deflected there, and the second abdominal lifting element runs from the deflecting element of the second intermediate region or of the second end region to the deflecting element of the second tensioning element and is deflected there, wherein the first abdominal elongated lifting element runs from the deflecting element of the first tensioning element in the direction of at least one of the end regions of the base body and wherein the second abdominal lifting element runs from the deflecting element of the second tensioning element in the direction of at least one of the end regions of the base body, and wherein the first end of the first abdominal lifting element and the first end of the second abdominal lifting element are each reversibly attachable onto the first end region of the base body and/or onto the second end region of the base body and/or onto the first end of the other abdominal lifting element, respectively.

* * * * *